United States Patent
Guinn et al.

(10) Patent No.: US 7,439,222 B2
(45) Date of Patent: Oct. 21, 2008

(54) PROCESS AND SYSTEMS FOR PEPTIDE SYNTHESIS

(75) Inventors: Martin R. Guinn, Golden, CO (US); Lewis M. Hodges, Longmont, CO (US); David A. Johnston, Louisville, CO (US); Hendrick Moorlag, Broomfield, CO (US); Mark A. Schwindt, Boulder, CO (US)

(73) Assignee: Roche Palo Alto LLC, Palo Alto, CA (US)

( * ) Notice: Subject to any disclaimer, the term of this patent is extended or adjusted under 35 U.S.C. 154(b) by 300 days.

(21) Appl. No.: 11/021,952

(22) Filed: Dec. 23, 2004

(65) Prior Publication Data

US 2005/0165217 A1  Jul. 28, 2005

Related U.S. Application Data

(60) Provisional application No. 60/533,654, filed on Dec. 31, 2003.

(51) Int. Cl.
*A01N 37/18* (2006.01)
*A61K 38/00* (2006.01)

(52) U.S. Cl. .......................................... 514/2
(58) Field of Classification Search .................. None
See application file for complete search history.

(56) References Cited

U.S. PATENT DOCUMENTS

| | | | |
|---|---|---|---|
| 4,108,846 | A | 8/1978 | Meienhofer |
| 5,126,273 | A | 6/1992 | Sheppard et al. |
| 5,356,596 | A | 10/1994 | Nokihara et al. |
| 5,464,933 | A | 11/1995 | Bolognesi et al. |
| 5,656,480 | A | 8/1997 | Wild et al. |
| 5,827,825 | A | 10/1998 | Takei et al. |
| 6,013,462 | A | 1/2000 | Kauvar et al. |
| 6,015,881 | A | 1/2000 | Kang et al. |
| 6,281,331 | B1 | 8/2001 | Kang et al. |
| 6,469,136 | B1 | 10/2002 | Bray et al. |
| 6,479,055 | B1 | 11/2002 | Bolognesi et al. |
| 2003/0125516 | A1 | 7/2003 | Bray et al. |

FOREIGN PATENT DOCUMENTS

| | | |
|---|---|---|
| WO | WO 90/02605 | 3/1990 |
| WO | WO 95/12608 | 5/1995 |
| WO | WO 93/25571 | 9/1995 |
| WO | WO 98/25965 | 6/1998 |
| WO | WO 99/46283 | 9/1999 |
| WO | WO 99/48513 | 9/1999 |

OTHER PUBLICATIONS

Vojkovsky. Detection of Secondary Amines on Solid Phase. Peptide Research. 1995, vol. 8., No. 4, pp. 236-237.*
Kaiser et al. Color Test for Detection of Free Terminal Amino Groups in the Solid-Phase Synthesis of Peptides. Analytical Biochemistry., 1970. vol. 34, No. 2, pp. 595-598.*
Riniker et al. (1993) Tetrahedron Letters 49:9307-9320.
Lloyd Williams et al. (1993) Tetrahedron Letters 49:11065-11133.
Bray, Brian L. (Jul. 2003) Nature Review 2:587-593.
Andersson et al. (2000) Biopolymers 55:227-250.
CA 132:279509 (abstract).
CA 132:276545 Meldal, M. et al (abstract).
Meldal (1994) *The Susceptibility of Glycans to b-elimination in Fmoc-based O-glycopeptide synthesis*, International Journal of Peptide and Protein Research, 43:529-536.

* cited by examiner

*Primary Examiner*—Cecilia J Tsang
*Assistant Examiner*—Marcela M Cordero Garcia
(74) *Attorney, Agent, or Firm*—Brian L. Buckwalter

(57) ABSTRACT

The invention provides methods of synthesizing peptides, involving the steps of providing a composition including a peptide fragment, wherein the peptide fragment has at least one amino acid residue and includes a base-sensitive, N-terminal protecting group; removing the base-sensitive, N-terminal protecting group from the peptide fragment using a deprotection reagent that includes a base, whereby an N-terminal functionality on the peptide fragment is deprotected; removing the base from the composition to provide a residual base content of more than 100 ppm; causing a reactive peptide fragment having a reactive C-terminus and a base-sensitive N-terminal protecting group to react with the deprotected N-terminal functionality of the peptide fragment under conditions such that the reactive peptide fragment is added to the peptide fragment; and optionally repeating the deprotection and coupling steps until a desired peptide is obtained. Also provided are methods of synthesizing peptides, wherein base is removed from the composition to a point where the composition would provide a positive chloranil test. Also provided are methods of synthesizing peptides, wherein coupling is performed in basic reaction mixtures.

33 Claims, No Drawings

SEQUENCE LISTING

<160> NUMBER OF SEQ ID NOS: 19

<210> SEQ ID NO 1
<211> LENGTH: 36

```
<212> TYPE: PRT
<213> ORGANISM: Human immunodeficiency virus

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 8
<212> TYPE: PRT
<213> ORGANISM: Artificial Sequence
<220> FEATURE:
<223> OTHER INFORMATION: Chemically synthesized peptide fragment

<400> SEQUENCE: 2

Tyr Thr Ser Leu Ile His Ser Leu
1               5

<210> SEQ ID NO 3
<211> LENGTH: 15
<212> TYPE: PRT
<213> ORGANISM: Artificial Sequence
<220> FEATURE:
<223> OTHER INFORMATION: Chemically synthesized peptide fragment

<400> SEQUENCE: 3

Tyr Thr Ser Leu Ile His Ser Leu Ile Glu Glu Ser Gln Asn Gln
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Chemically synthesized peptide fragment

<400> SEQUENCE: 4

Tyr Thr Ser Leu Ile His Ser Leu Ile Glu Glu Ser Gln Asn Gln Gln
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Chemically synthesized peptide fragment

<400> SEQUENCE: 5

Tyr Thr Ser Leu Ile His Ser Leu Ile Glu Glu Ser Gln Asn Gln Gln
1               5                   10                  15

Glu Lys

<210> SEQ ID NO 6
<211> LENGTH: 7
<212> TYPE: PRT
<213> ORGANISM: Artificial Sequence
<220> FEATURE:
<223> OTHER INFORMATION: Chemically synthesized peptide fragment

<400> SEQUENCE: 6

Ile Glu Glu Ser Gln Asn Gln
```

```
<210> SEQ ID NO 7
<211> LENGTH: 8
<212> TYPE: PRT
<213> ORGANISM: Artificial Sequence
<220> FEATURE:
<223> OTHER INFORMATION: Chemically synthesized peptide fragment

<400> SEQUENCE: 7

Ile Glu Glu Ser Gln Asn Gln Gln
1               5

<210> SEQ ID NO 8
<211> LENGTH: 20
<212> TYPE: PRT
<213> ORGANISM: Artificial Sequence
<220> FEATURE:
<223> OTHER INFORMATION: Chemically synthesized peptide fragment

<400> SEQUENCE: 8

Gln Glu Lys Asn Glu Gln Glu Leu Leu Glu Leu Asp Lys Trp Ala Ser
1               5                   10                  15

Leu Trp Asn Trp
            20

<210> SEQ ID NO 9
<211> LENGTH: 21
<212> TYPE: PRT
<213> ORGANISM: Artificial Sequence
<220> FEATURE:
<223> OTHER INFORMATION: Chemically synthesized peptide fragment

<400> SEQUENCE: 9

Gln Glu Lys Asn Glu Gln Glu Leu Leu Glu Leu Asp Lys Trp Ala Ser
1               5                   10                  15

Leu Trp Asn Trp Phe
            20

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized peptide fragment

<400> SEQUENCE: 10

Glu Lys Asn Glu Gln Glu Leu
1               5

<210> SEQ ID NO 11
<211> LENGTH: 10
<212> TYPE: PRT
<213> ORGANISM: Artificial Sequence
<220> FEATURE:
<223> OTHER INFORMATION: Chemically synthesized peptide fragment

<400> SEQUENCE: 11

Glu Lys Asn Glu Gln Glu Leu Leu Glu Leu
1               5                   10

<210> SEQ ID NO 12
<211> LENGTH: 20
<212> TYPE: PRT
<213> ORGANISM: Artificial Sequence
<220> FEATURE:
```

```
<223> OTHER INFORMATION: Chemically synthesized peptide fragment

<400> SEQUENCE: 12

Glu Lys Asn Glu Gln Glu Leu Leu Glu Leu Asp Lys Trp Ala Ser Leu
1               5                   10                  15

Trp Asn Trp Phe
            20

<210> SEQ ID NO 13
<211> LENGTH: 17
<212> TYPE: PRT
<213> ORGANISM: Artificial Sequence
<220> FEATURE:
<223> OTHER INFORMATION: Chemically synthesized peptide fragment

<400> SEQUENCE: 13

Asn Glu Gln Glu Leu Leu Glu Leu Asp Lys Trp Ala Ser Leu Trp Asn
1               5                   10                  15

Trp

<210> SEQ ID NO 14
<211> LENGTH: 18
<212> TYPE: PRT
<213> ORGANISM: Artificial Sequence
<220> FEATURE:
<223> OTHER INFORMATION: Chemically synthesized peptide fragment

<400> SEQUENCE: 14

Asn Glu Gln Glu Leu Leu Glu Leu Asp Lys Trp Ala Ser Leu Trp Asn
1               5                   10                  15

Trp Phe

<210> SEQ ID NO 15
<211> LENGTH: 12
<212> TYPE: PRT
<213> ORGANISM: Artificial Sequence
<220> FEATURE:
<223> OTHER INFORMATION: Chemically synthesized peptide fragment

<400> SEQUENCE: 15

Leu Glu Leu Asp Lys Trp Ala Ser Leu Trp Asn Trp
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Chemically synthesized peptide fragment

<400> SEQUENCE: 16

Leu Glu Leu Asp Lys Trp Ala Ser Leu Trp Asn Trp Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized peptide fragment

<400> SEQUENCE: 17

Asp Lys Trp Ala Ser Leu Trp Asn Trp
1               5
```

```
<210> SEQ ID NO 18
<211> LENGTH: 10
<212> TYPE: PRT
<213> ORGANISM: Artificial Sequence
<220> FEATURE:
<223> OTHER INFORMATION: Chemically synthesized peptide fragment

<400> SEQUENCE: 18

Asp Lys Trp Ala Ser Leu Trp Asn Trp Phe
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Chemically synthesized peptide fragment

<400> SEQUENCE: 19

Glu Lys Asn Glu Gln Glu Leu Leu Glu Leu Asp Lys Trp Ala Ser Leu
1               5                   10                  15

Trp Asn Trp
```

PROCESS AND SYSTEMS FOR PEPTIDE SYNTHESIS

PRIORITY CLAIM

The present non-provisional patent Application claims priority under 35 USC §119(e) from U.S. Provisional Patent Application having Ser. No. 60/533,654, filed on Dec. 31, 2003, and titled PROCESS AND SYSTEMS FOR PEPTIDE SYNTHESIS, wherein said provisional patent application is commonly owned by the owner of the present patent application and wherein the entire contents of said provisional patent application is incorporated herein by reference.

FIELD OF THE INVENTION

The invention relates to synthesis of peptides. More particularly, the invention relates to the steps of deprotection and amino acid coupling during synthesis of peptides.

BACKGROUND OF THE INVENTION

Many methods for peptide synthesis are described in the literature (for examples, see U.S. Pat. No. 6,015,881; Mergler et al. (1988) Tetrahedron Letters 29:4005-4008; Mergler et al. (1988) Tetrahedron Letters 29:4009-4012; Kamber et al. (eds), Peptides, Chemistry and Biology, ESCOM, Leiden (1992) 525-526; Riniker et al. (1993) Tetrahedron Letters 49:9307-9320; Lloyd-Williams et al. (1993) Tetrahedron Letters 49:11065-11133; and Andersson et al. (2000) Biopolymers 55:227-250; Bray, Brian L., Nature Reviews 2:587-593 (2003). The various methods of synthesis are distinguished by the physical state of the phase in which the synthesis takes place, namely liquid phase or solid phase.

Liquid phase methods (often referred to as solution phase methods) of synthesis carry out all reactions in a homogeneous phase. Successive amino acids are coupled in solution until the desired peptide material is formed. During synthesis, successive intermediate peptides are purified by precipitation and/or washes.

In solid phase peptide synthesis (SPPS), a first amino acid or peptide group is bound to an insoluble support, such as a resin. Successive amino acids or peptide groups are added to the first amino acid or peptide group until the peptide material of interest is formed. The product of solid phase synthesis is thus a peptide bound to an insoluble support. Peptides synthesized via SPPS techniques are then cleaved from the resin, and the cleaved peptide is isolated.

In addition to the liquid phase and SPPS techniques described above, a hybrid approach can be utilized. Hybrid synthesis is typically utilized to manufacture complex sequences. For example, in one representative hybrid scheme, complex sequences can be manufactured through the solid phase synthesis of protected peptide intermediates, which are subsequently assembled either by solution phase or SPPS methods to produce a longer peptide product. Thus, for example, as a step in the synthesis, an intermediate compound is produced that includes each of the amino acid residues located in its desired sequence in the peptide chain with various of these residues having side chain protecting groups. The protected peptide intermediates are then coupled in solution to form a longer peptide. See, for example, WO 99/48513.

Peptides and amino acids from which peptides are synthesized tend to have reactive side groups as well as reactive terminal ends. When synthesizing a peptide, it is important that the amino group on one peptide react with the carboxyl group on another peptide. Undesired reactions at side groups or at the wrong terminal end of a reactant produces undesirable by-products, sometimes in significant quantities. These can seriously impair yield or even ruin the product being synthesized from a practical perspective. To minimize side reactions, it is conventional practice to appropriately mask reactive side groups and terminal ends of reactants to help ensure that the desired reaction occurs.

For example, a typical solid phase synthesis scheme involves attaching a first amino acid or peptide group to a support resin via the carboxyl moiety of the peptide or amino acid. This leaves the amino group of the resin-bound material available to couple with additional amino acids or peptide material. Thus, the carboxyl moiety of the additional amino acid or peptide material desirably reacts with the free amino group of the resin-bound material. To avoid side reactions involving the amine group of the additional amino acid or peptide, such amine group is masked with a protecting group during the coupling reaction. Two well-known amine protecting groups are the BOC group and the FMOC group. Many others have also been described in the literature. After coupling, the protecting group on the N-terminus of the resin-bound peptide can be removed, allowing additional amino acids or peptide material to be added to the growing chain in a similar fashion. In the meantime, reactive side chain groups of the amino acid and peptide reactants, including the resin-bound peptide material as well as the additional material to be added to the growing chain, typically remain masked with side chain protecting groups throughout synthesis. These same concepts (without a support resin for the initial amino acid) can be applied to liquid phase synthesis techniques.

The step of removing protecting groups from a peptide is commonly referred to as deprotection. When all of the protecting groups (including terminal protecting groups and side chain protecting groups) are removed, this is referred to as global deprotection. In some cases, only the N-terminal protecting group is removed. The reagents utilized in N-terminal deprotection typically leave the side chain protecting groups intact. In one exemplary N-terminal deprotection scheme, the removal of the N-terminal protecting group (for example, an Fmoc group) is typically accomplished by treatment with a reagent that includes 20-50% (on a weight basis) piperidine in a solvent, such as N-methylpyrrolidone (NMP) or dimethylformamide (DMF). After removal of the Fmoc protecting group, several washes are typically performed to remove residual piperidine and Fmoc by-products (such as dibenzofulvene and its piperidine adduct). Conventional synthesis techniques have stressed the importance of removing residual piperidine, to reduce unwanted reactions, such as premature removal of Fmoc protecting groups on subsequent amino acids to be added to the peptide chain. In other words, it has been recognized that the Fmoc group should remain on amino acids until the particular amino acid has been incorporated into a growing peptide material and is ready to be activated for coupling to a subsequent amino acid.

Several tests have been developed to determine when the removal of Fmoc by-products and residual piperidine from a reaction solution is complete. The most common of these tests is the chloranil test, which utilizes a saturated solution of chloranil and toluene in acetone. Color is used to determine the presence of secondary amine (thus indicating that Fmoc by-products and/or residual piperidine are still present). Other tests involve monitoring the pH of the reaction solution to determine the presence of piperidine (for example, using pH paper). Still other tests involve including a dye with the deprotection reagent, and monitoring the color of the reaction solution visually to determine when the dye (and thus deprotection reagent) has been removed from the reaction solution. Once the Fmoc protecting group is removed, an additional activated amino acid residue can be added to the peptide fragment, and the cycle repeated for subsequent amino acid residues until the desired peptide is completed.

For large-scale production of peptides, issues relating to reagent consumption, as well as cycle and processing time, can greatly impact the feasibility of the peptide synthesis scheme. Thus, there is a continuing need for peptide synthesis processes capable of producing peptide materials of commercial interest in large batch quantities. Deprotection of amino acid residues at the N-terminus to allow coupling of an additional amino acid, for example, by treatment with a base, is one aspect of the synthesis in which improvement is needed. Conventional methodologies may utilize reagents at levels that are higher than desirable and involve additional processing steps that are unnecessary.

SUMMARY OF THE INVENTION

The invention relates to methods for the synthesis of peptide material (peptides and peptide intermediates), in particular methods involving synthesis of peptide material with reduced reagent usage, reaction mixture volumes, and cycle and processing time. Generally speaking, the inventive methods are applicable to the deprotection and coupling steps of peptide synthesis. More specifically, the invention relates to the use and presence of deprotection reagent during the deprotection and coupling steps of synthesis.

In one aspect of the invention, it has been surprisingly discovered that significantly higher levels of deprotection reagent can be tolerated in subsequent processing steps of peptide synthesis. For example, it has been discovered that more residual base can be tolerated in reactions subsequent to deprotection, where peptide material is added at the C-terminal portion of a peptide fragment without the base undermining the N-terminal protection of the peptide material being added. In this aspect, the invention provides peptide synthesis processes that involve coupling reactions with novel characteristics. For instance, in one embodiment, the coupling reaction mixture is basic with respect to pH. As described herein, the synthesis reactions to which the inventive methods are particularly applicable involve a base (such as piperidine) as the deprotection reagent. The presence of higher amounts of deprotection agent in the composition during coupling reactions will thus provide a more basic composition. In other embodiments, the coupling reaction mixture includes a residual base content of more than 100 ppm (weight basis), which is significantly higher than conventional synthesis techniques allow. For instance, conventional synthesis techniques require removal of residual piperidine and Fmoc by-products (dibenzofulvene and its piperidine adduct) before coupling of a subsequent amino acid. To this end, testing is performed to ensure no residual piperidine is left in the reaction mixture before the subsequent amino acid is added to the reaction system. As described herein, conventional tests that have been developed to monitor removal of piperidine can identify: (a) the presence of secondary amines in the reaction mixture (for example, a chloranil test); (b) a neutral pH of the reaction mixture (for example, using pH paper or other pH monitor); and/or (c) the presence of dyes that are included in the deprotection reagent (for example, coupled to the deprotection reagent). In still further embodiments of the invention, the coupling reaction is performed in a reaction mixture that would provide a positive test if subjected to a chloranil test.

According to some aspects of the invention, reagents are required in lesser amounts to remove the deprotection reagent before the coupling step is performed. Preferably, the inventive methods eliminate processing steps by reducing the number of washing steps required for removal of the deprotection reagent. Elimination of washing steps can substantially reduce overall processing time and cycle time, which can increase overall synthesis capacity. The inventive methods can reduce the amount of washing solvent required by as much as 50%. This can result in significant savings in raw material cost per kilogram of peptide product produced.

In one aspect, the inventive methods utilize significantly less deprotection reagent to remove N-terminal protecting groups during the deprotection step. For instance, conventional synthesis techniques might utilize a solution containing 20-50% piperidine (on a weight basis) in a solvent such as NMP or DMF. For solid phase synthesis, the concentration of piperidine can be in the lower portion of this concentration range (for example, 20-30% piperidine in solvent), whereas in liquid phase synthesis, the concentration can be in the upper portion of this concentration range (for example, 30% or more piperidine in solvent). In contrast, some embodiments of the inventive methods can utilize deprotection reagent that includes piperidine in an amount less than 20%, or less than 10%, or about 5% (on a weight basis). In preferred embodiments, the inventive methods utilize a deprotection reagent that includes piperidine in an amount in the range of about 5% to about 10% (on a weight basis).

According to these aspects of the invention, the inventive methods allow significant reduction in reagent usage during synthesis, and this reduced reagent usage can provide significant advantages in large-scale peptide synthesis. Substantially less starting material can be used in the form of the deprotection reagent, which can result in substantial cost savings. In turn, less of the deprotection reagent will be present in the reaction mixture after deprotection is complete and before coupling can be performed. The inventive methods thus require fewer washes to remove the deprotection reagent after N-terminal protecting group cleavage. Reduced washes can translate into less reagent usage and reduced cycle and processing times in the overall synthesis.

As will be apparent upon review of the present description, embodiments of the invention can include performance of peptide synthesis reactions subsequent to deprotection in reaction mixtures that exhibit higher deprotection agent levels, utilization of less deprotection agent in peptide synthesis reactions, or a combination of these aspects. In any of the embodiments described herein, the inventive methods can surprisingly provide comparable yield and fragment purity as conventional methods.

In one aspect, the invention provides a method of synthesizing a peptide, comprising steps of: (a) providing a composition comprising a peptide fragment, wherein the peptide fragment comprises at least one amino acid residue and includes a base-sensitive, N-terminal protecting group; (b) removing the base-sensitive, N-terminal protecting group from the peptide fragment using a deprotection reagent comprising a base, whereby an N-terminal functionality on the peptide fragment is deprotected; (c) removing the base from the composition to provide a residual base content of more than 100 ppm; (d) causing a reactive peptide fragment having a reactive C-terminus and a base-sensitive N-terminal protecting group to react with the deprotected N-terminal functionality of the peptide fragment under conditions such that the reactive peptide fragment is added to the peptide fragment; and (e) optionally repeating steps (b) through (d) until a desired peptide is obtained.

In another aspect, the invention provides a method of synthesizing a peptide, comprising steps of: (a) providing a composition comprising a peptide fragment, wherein the peptide fragment comprises at least one amino acid residue and includes a base-sensitive, N-terminal protecting group; (b) removing the base-sensitive, N-terminal protecting group from the peptide fragment using a deprotection reagent comprising a base, whereby an N-terminal functionality on the peptide fragment is deprotected; (c) removing the base from the composition to a point where the composition would provide a positive test result if subjected to a chloranil test; (d) causing a reactive peptide fragment having a reactive C-terminus and a base-sensitive N-terminal protecting group to react with the deprotected N-terminal functionality of the peptide fragment under conditions such that the reactive peptide fragment is added to the peptide fragment; and (e) optionally repeating steps (b) through (d) until a desired peptide is obtained.

In yet another aspect, the invention provides a method of synthesizing a peptide, comprising steps of: (a) providing a composition comprising a peptide fragment, wherein the peptide fragment comprises at least one amino acid residue and includes a base-sensitive, N-terminal protecting group; (b) removing the base-sensitive N-terminal protecting group from the amino acid residue using a deprotection reagent comprising a base, whereby an N-terminal functionality on the peptide fragment is deprotected; (c) causing a reactive peptide fragment having a reactive C-terminus and a base-sensitive, N-terminal protecting group to react with the deprotected N-terminal functionality of the peptide fragment under conditions such that the reactive peptide fragment is added to the peptide fragment, wherein the composition has a basic pH during the reaction of the reactive peptide fragment and the peptide fragment; and (d) optionally repeating steps (b) and (c) until a desired peptide is obtained.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The present invention is directed to methods for effectively synthesizing peptides and peptide intermediates, and in particular for effectively removing base-sensitive N-terminal protecting groups to thereby form an N-terminal deprotected amino acid (an N-alpha amino group), and subsequently coupling an amino acid to the N-alpha amino group.

The methods described herein are particularly suitable for improving aspects of scaled-up synthesis of peptides. In preferred embodiments, the inventive methods can provide such improvements as reduction in processing and cycling time, as well as reduction in amount of reagents and starting materials required.

The processes of the present invention can be used in connection with the synthesis of peptides of any suitable length and/or sequence. It will be understood that the peptides of the invention can be synthesized or prepared by techniques well known in the art. See, for example, Creighton, 1983, Proteins: Structures and Molecular Principles, W. H. Freeman and Co., NY, as well as additional references cited herein. Residues of one or more other monomeric, oligomeric, and/or polymeric constituents optionally can be incorporated into a peptide. Non-peptide bonds may also be present. These non-peptide bonds can be between amino acid residues, between an amino acid and a non-amino acid residue, or between two non-amino acid residues. These alternative non-peptide bonds can be formed by utilizing reactions well known to those in the art, and may include, but are not limited to, imino, ester, hydrazide, semicarbazide, azo bonds, and the like.

As used herein, the term "monomer" means a relatively low molecular weight material (i.e., generally having a molecular weight less than about 500 Daltons) having one or more polymerizable groups. "Oligomer" means a relatively intermediate sized molecule incorporating two or more monomers and generally having a molecular weight of from about 500 up to about 10,000 Daltons. "Polymer" means a relatively large material comprising a substructure formed two or more monomeric, oligomeric, and/or polymeric constituents and generally having a molecular weight greater than about 10,000 Daltons.

The amino acids from which the peptides are derived can be naturally occurring amino acid residues, non-natural amino acid residues, or combinations thereof. The twenty common naturally-occurring amino acid residues are as follows: A (Ala, alanine), R (Arg, arginine); N (Asn, asparagine); D (Asp, aspartic acid); C (Cys, cysteine) Q (Gln, glutamine), E (Glu, glutamic acid); G (Gly, glycine); H (His, histidine); I (Ile, isoleucine); L (Leu, leucine); K (Lys, lysine); M (Met, methionine); F (Phe, phenylalanine); P (Pro, proline); S (Ser, serine); T (Thr, threonine); W (Trp, tryptophan); Y (Tyr, tyrosine); and V (Val, valine). Naturally occurring rare amino acids are also contemplated and include, for example, selenocysteine and pyrrolysine.

Non-natural amino acids include organic compounds having a similar structure and reactivity to that of naturally-occurring amino acids and include, for example, D-amino acids, beta amino acids, omega-amino acids (such as 3-aminopropionic acid, 2,3-diaminopropionic acid, 4-aminobutyric acid, and the like), gamma amino acids, cyclic amino acid analogs, proparglycine derivatives, 2-amino-4-cyanobutyric acid derivatives, Weinreb amides of α-amino acids, and amino alcohols.

The present invention contemplates that the synthesized peptide material may act as intermediates in the synthesis of other peptides of interest through modification of the resultant peptide, through coupling of the peptide to other materials such as other peptides, or the like. For example, the present invention would be particularly useful to synthesize peptide fragment intermediates useful in the synthesis of enfuvirtide (also known as the T-20 peptide), or alternatively DP-178. Such peptide fragments of the invention include, but are not limited to, those having amino acid sequences as depicted in Table 1 below:

TABLE 1

| PEPTIDE NO. | AMINO ACID SEQUENCE | SEQ ID NO | CORRESPONDING AMINO ACID SEQUENCE OF T-20 |
|---|---|---|---|
| 1 | YTSLIHSL | (SEQ ID NO:2) | 1-8 |
| 2 | YTSLIHSLIEESQNQ | (SEQ ID NO:3) | 1-15 |
| 3 | YTSLIHSLIEESQNQQ | (SEQ ID NO:4) | 1-16 |
| 4 | YTSLIHSLIEESQNQQEK | (SEQ ID NO:5) | 1-18 |
| 5 | IEESQNQ | (SEQ ID NO:6) | 9-15 |
| 6 | IEESQNQQ | (SEQ ID NO:7) | 9-16 |
| 7 | QEKNEQELLELDKWASLWNW | (SEQ ID NO:8) | 16-35 |

TABLE 1-continued

| PEP-TIDE NO. | AMINO ACID SEQUENCE | SEQ ID NO | CORRESPONDING AMINO ACID SEQUENCE OF T-20 |
|---|---|---|---|
| 8 | QEKNEQELLELDKWASLWNWF | (SEQ ID NO:9) | 16-36 |
| 9 | EKNEQEL | (SEQ ID NO:10) | 17-23 |
| 10 | EKNEQELLEL | (SEQ ID NO:11) | 17-26 |
| 11 | EKNEQELLELDKWASLWNWF | (SEQ ID NO:12) | 17-36 |
| 12 | NEQELLELDKWASLWNW | (SEQ ID NO:13) | 19-35 |
| 13 | NEQELLELDKWASLWNWF | (SEQ ID NO:14) | 19-36 |
| 14 | LELDKWASLWNW | (SEQ ID NO:15) | 24-35 |
| 15 | LELDKWASLWNWF | (SEQ ID NO:16) | 24-36 |
| 16 | DKWASLWNW | (SEQ ID NO:17) | 27-35 |
| 17 | DKWASLWNWF | (SEQ ID NO:18) | 27-36 |
| 18 | EKNEQELLELDKWASLWNW | (SEQ ID NO:19) | 17-35 |

Enfuvirtide is a peptide that corresponds to amino acid residues 638 to 673 of the transmembrane protein gp41 from HIV-1.sub.LAI isolate and has the 36 amino acid sequence (reading from amino, NH$_2$ to carboxy, COOH, terminus):
NH$_2$-YTSLIHSLIEESQNQQEKNEQELLELDK-WASLWNWF-COOH (SEQ ID NO:1)

The chemical name of enfuvirtide is N-acetyl-Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Ala-Ser-Leu-Trp-Asn-Trp-Phe-CONH$_2$. It will be understood that the principles of the present invention may also be applied in preferred embodiments to the recovery of peptides constituting all or a portion of T-20-like peptide fragments in addition to T-20 peptide fragments. The term "T-20-like" as used herein includes any HIV or non-HIV peptide listed in U.S. Pat. Nos. 5,464,933; 5,656,480, 6,015,881, 6,281,331, or PCT Publication No. WO 96/19495. The synthesis of peptides having T-20 activity and peptide intermediates used to prepare peptides having T-20 activity are described in U.S. Pat. Nos. 5,464,933; 5,656,480, 6,015,881, 6,281,331, and PCT Publication No. WO 96/19495.

In addition to peptides useful in the synthesis of enfuvirtide and enfuvirtide-like peptides, the principles of the present invention may be advantageously used to synthesize the following peptide material, fragment intermediates thereof, and/or analogs: oxytocin; vasopressin analogues such as Felypressin, Pitressin, Lypressin, Decompression, Perlipression; Atosiban; adrenocorticotropic hormone (ACTH); Insulin, Glucagon; Secretin; calcitoninins: human calcitonin, salmon calcitonin, eel calcitonin, dicarba-eel (elcatonin); luteinizing hormone-releasing hormone (LH-RH) and analogues: leuprolide, deslorelin, triptorelin, goserelin, buserelin; nafarelin, cetrorelix, ganirelix, parathyroid hormone (PTH); human corticotrophin-releasing factor, ovine corticotrophin-releasing factor; growth hormone releasing factor; somatostatin; lanreotide, octretide, thyrotripin releasing hormone (TRH); thymosin -1; thomopentin (TP-5); cyclosporin; integrilin; angiotensin-converting enzyme inhibitors: enalapril, lisinopril.

The invention contemplates synthesis of peptides that have been chemically altered to contain one or more chemical groups other than amino acid residues, sometimes referred to as modified peptides. Such chemical groups can be included at the amino termini of the peptides, the carboxy termini, and/or at one or more amino acid residues along the length of the peptide. In still further embodiments, the peptide can include additional chemical groups present at their amino and/or carboxy termini, such that, for example, the stability, reactivity and/or solubility of the peptides are enhanced. For example, hydrophobic groups such as carbobenzoxyl, dansyl, or acetyl groups can be added to the amino termini of peptides. Similarly, a para-nitrobenzyl ester group can be placed at the carboxy termini of peptides. Techniques for introducing such modifications are well known in the art.

In some aspects, the invention provides methods of synthesizing peptides that can include one or more protecting groups. The nature and use of protecting groups is well known in the art. Generally, a suitable protecting group is any sort of group that can help prevent the atom to which it is attached, typically oxygen or nitrogen, from participating in undesired reactions during processing and synthesis. Protecting groups include side chain protecting groups and amino- or N-terminal protecting groups. Protecting groups can also prevent reaction or bonding of carboxylic acids, thiols, and the like.

A side chain protecting group refers to a chemical moiety coupled to the side chain (R group in the general amino acid formula H$_2$N—C(R)(H)—COOH) of an amino acid that helps prevent a portion of the side chain from reacting with chemicals used in steps of peptide synthesis, processing, and the like. The choice of a side chain protecting group can depend upon various factors, for example, the type of synthesis performed, processing to which the peptide will be subjected, and the desired intermediate product or final product. The side chain protecting group also depends upon the nature of the amino acid itself. Generally, a side chain protecting group is chosen that is not removed during deprotection of the α-amino groups during synthesis. Therefore, the α-amino protecting group and the side chain protecting group are typically not the same.

In some cases, and depending upon the type of reagents used in solid phase synthesis and other peptide processing, an amino acid may not require the presence of a side chain protecting group. Such amino acids typically do not include a reactive oxygen or nitrogen in the side chain.

Examples of side chain protecting groups include acetyl (Ac), benzoyl (Bz), tert butyl, triphenylmethyl (trityl), tetrahydropyranyl, benzyl ether (Bzl), 2,6-dichlorobenzyl (DCB), t-butoxycarbonyl (BOC), nitro, p-toluenesulfonyl (Tos), adamantyloxycarbonyl, xanthyl (Xan), benzyl, methyl, ethyl, and t-butyl ester, benzyloxycarbonyl (Z), 2-chlorobenzyloxycarbonyl (2-Cl-Z), t-amyloxycarbonyl (Aoc), and aromatic or aliphatic urethan-type protecting groups, photolabile groups such as nitro veratryl oxycarbonyl (NVOC), and fluoride labile groups such as trimethylsilylethyl oxycarbonyl (TEOC).

For example, any one or more of the side chains of the amino acid residues of peptide fragments listed in Table 1 can be protected with standard protecting groups such as t-butyl (t-Bu), trityl (trt), and t-buyloxycarbonyl (Boc). Preferred side chain protecting groups include the t-Bu group for tyrosine, threonine, serine and aspartic acid amino acid residues; the trt group for histidine, glutamine, and asparagine amino acid residues; and the Boc group for lysine and tryptophan amino acid residues.

During the synthesis of fragments of Table 1 that include histidine, the side chain of the histidine residue desirably is protected, preferably with a trityl (trt) protecting group. If the histidine residue is not protected, reagents utilized in synthesis and processing of peptides (for example, the acid used to cleave the peptide fragment from the resin in solid phase synthesis) could detrimentally react with the histidine residue, causing degradation of the peptide fragment.

Preferably, the glutamine residues of the peptide fragments of the invention are protected with trityl (trt) groups. However, it is preferred not to protect the glutamine residue at the carboxy-terminal end of fragments 1-16 and 9-16. It has been found that the absence of a protective group on the glutamine residue at the carboxy-terminal end of the 1-16 fragment facilitates reaction of the 1-16 fragment with the 17-36 fragment, allowing coupling of the fragments with only about 2% racemization. In addition, if lower solubility of any of the peptide fragments of the invention in organic solvents is desired, the trityl protecting groups may be eliminated from any one or more of the other glutamine residues of the fragments.

Preferably, all the asparagine residues of each peptide fragment of the invention are protected. In addition, it is preferred that the tryptophan residue is protected with a Boc group.

An amino terminal protecting group (also referred to as an N-terminal protecting group) includes a chemical moiety coupled to the alpha amino group of an amino acid. Typically, the amino terminal protecting group is removed in a deprotection reaction prior to the addition of the next amino acid to be added to the growing peptide chain, but can be maintained when the peptide is cleaved from the support during solid phase synthesis. The amino terminal group can be maintained when washing or otherwise processing the peptide as well. The choice of an amino terminal protecting group can depend upon various factors, for example, the type of synthesis performed and the desired intermediate product or final product obtained.

Examples of amino terminal protecting groups (also referred to herein as N-terminal protecting groups) include: (1) acyl-type protecting groups, such as formyl, acrylyl (Acr), benzoyl (Bz) and acetyl (Ac); (2) aromatic urethan-type protecting groups, such as benzyloxycarbonyl (Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl; and (5) thiourethan-type protecting groups, such as phenylthiocarbonyl. Preferred protecting groups include 9-fluorenylmethyloxycarbonyl (Fmoc), 2-(4-biphenylyl)-propyl(2)oxycarbonyl (Bpoc), 2-phyenlpropyl(2)-oxycarbonyl (Poc), and t-butyloxycarbonyl (Boc). A preferred amino terminal protecting group is Fmoc.

According to the invention, preferred protecting groups include Boc and Fmoc.

In an initial step of the invention, a composition comprising a peptide fragment is provided, wherein the peptide fragment comprises at least one amino acid residue and includes a base-sensitive, N-terminal protecting group. As used herein, a base-sensitive, N-terminal protecting group refers to a protecting group that can be de-coupled from the amino acid by a base. The base-sensitive N-terminal protecting group helps ensure amino acid coupling at the correct location and in the correct orientation (N→C or C→N). The choice of suitable base-sensitive protecting group for the N-terminus is not particularly limited, provided the protecting group is compatible with the reagents utilized in synthesis, including starting materials and solvents. Preferred N-terminal, base-sensitive protecting groups include cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl.

In the course of providing the peptide fragment composition, optionally, one or more side chain protecting groups, and/or C-terminal protecting groups can be provided on the peptide fragment. As described herein, however, such side chain and/or C-terminal protecting groups are optional only and are not required.

The invention involves removing the base-sensitive, N-terminal protecting group from the peptide fragment using a deprotection reagent comprising a base. Suitable bases include secondary amines and/or reagents that are capable of hydrogenolysis. Exemplary bases include piperidine, diethylamine, piperazine.

Typically, the deprotection reagent is provided in a solvent, such as NMP, DMF, and $CH_2Cl_2$.

Once the base-sensitive N-terminal protecting group has been removed by an appropriate deprotection reagent, the N-alpha-amino group of the deprotected amino acid is made available for forming a peptide bond with a suitable reactive peptide fragment. The deprotected peptide fragment is thus prepared for subsequent reaction and amide bond formation.

According to the invention, base is removed from the peptide composition to provide a reaction mixture suitable for subsequent processing (such as coupling). The present inventors have surprisingly discovered that not all residual base must be removed from the composition prior to subsequent processing. After deprotection, the reaction mixture can be basic with respect to pH for subsequent coupling and other processing. Broadly, basic characteristics of the reaction mixture can be assessed several ways. For example, the amount of base present in the reaction mixture can be determined on a weight basis (parts per million, ppm). A qualitative test, such as the chloranil test, can be performed to determine whether residual base is present in the reaction mixture. The pH of the reaction mixture can be determined to assess the basic characteristics of the reaction mixture.

According to the invention, the coupling reaction can be performed in reaction mixtures that exhibit novel features. For instance, the inventive methods include coupling reactions that include a residual base content of more than about 100 ppm, or in the range of about 100 ppm to about 10,000 ppm, or in the range of about 500 ppm to about 7,000 ppm (weight basis). As described herein, the residual base content of the inventive methods is significantly higher than prior peptide synthesis methods. The amount of residual base present in the coupling reaction can be monitored, for example by standard techniques known in the art.

In another embodiment, the coupling reaction can include a residual base content such that the coupling reaction would provide a positive test result if subjected to a chloranil test. Thus, the coupling reaction is performed in the presence of secondary amines (as a result of residual base and/or by-products). In yet further embodiments, the coupling reaction is performed in relatively basic conditions, preferably in conditions of moderately basic pH. In some embodiments, the pH of the reaction mixture during the coupling reaction is greater than 7, or in the range of 7.2 to 8.5, or in the range of 7.2 to 8. As described herein, many common methods for measuring pH of a composition are available, and any such method can be used in connection with the invention.

According to the invention, the N-terminal functionality of a peptide fragment is deprotected, making the N-terminus of the peptide fragment available for reacting with a reactive peptide fragment. As used herein, reactive peptide fragments include a base sensitive, N-terminal protecting group, a reactive C-terminus, and optionally a side chain protecting group. The reactive C-terminus is thus available to form a peptide bond with a deprotected N-alpha amino group of an additional peptide fragment.

Peptide bond formation involves activation of the carboxyl group of the reactive C-terminus. There are four major coupling techniques commonly utilized. The first coupling technique involves in situ coupling reagents such as carbodiimide-mediated coupling, BOP, o-(benzotriazol-1-yl)-N,N,N'N'-tetramethyluronium hexafluorophosphate (HBTU), and HATU, dicyclohexylcarbodiimide (DCC), water-soluble carbodiimide (WSCDI)), and uronium reagents (for example, o-(benzotriazol-1-yl)-N,N,N',N'-tetramethyluronium tetrafluoroborate (TBTU). A second coupling technique uses preformed active esters such as hydroxysuccinimide (HOSu) and p-nitrophenol (HONp) esters). A third coupling technique involves preformed symmetrical anhydrides, such as N-carboxyanhydrides (NCAs). Another technique uses acid halides such as acyl fluoride as well as acyl chloride. The preformed amino acid derivates can have the added benefits of not generating by-products from the activating agent and also of being compatible with an unprotected C-terminal amino acid residue in the amino component. For the carbodiimide and TBTU methods, however, C-terminal protection is preferable.

Solvents that are suitable for the coupling reaction include dichloromethane (DCM), dichloroethane (DCE), dimethylformamide (DMF), methylene chloride, and the like, as well as mixtures of these reagents. Other useful solvents include DMSO, pyridine, chloroform, dioxane, tetrahydrofuran, ethyl acetate, N-methylpyrrolidone, and mixtures thereof.

The reactive peptide fragment can include one amino acid residue, or a peptide containing more than one amino acid residue, as desired. In some embodiments, peptides that include more than one amino acid residue are coupled. When coupling peptides, the risk for racemization is increased, due to the possibility of oxazolone formation. However, several techniques are available to help prevent racemization by providing a protecting reagent. One of the most common involves carbodiimide (for example, DCC or WSCDI) with an added auxiliary nucleophile (for example, 1-hydroxy-benzotriazole (HOBt), 1-hydroxy-azabenzotriazole (HOAt), or HOSu). Another reagent that can be utilized is TBTU. The mixed anhydride method, using isobutyl chloroformate, with or without an added auxiliary nucleophile, is also utilized, as is the azide method, due to the low racemization associated with it. These types of compounds can also increase the rate of carbodiimide-mediated couplings, as well as prevent dehydration of Asn and Gln residues. Other compounds that can increase the rate of reaction and reduce the rate of side reactions include phosphonium and uronium salts that can, in the presence of a tertiary base, convert protected amino acids into activated species (for example, BOP, PyBOPO, HBTU, and TBTU all generate HOBt esters).

According to the invention, the reactive peptide fragment is activated to provide a reactive carboxy terminus. In an exemplary activation process, an Fmoc-protected amino acid, HOBT, and DIEA are dissolved in an inert solvent (such as NMP) at room temperature. The solution is then chilled to approximately 0-5° C., and then HBTU is added and the reaction solution is stirred for an appropriate time to dissolve the HBTU. It has been found that activation and racemization are controlled by adding the HBTU last to the cold solution.

The peptide fragment is now ready for coupling to another peptide fragment that includes a deprotected N-terminal functionality.

The reactive peptide fragment is added to a coupling mixture that includes the deprotected peptide fragment. The coupling reaction typically utilizes a stoichiometric excess of amino acids, for example, 1.3 or more, 2 or more, or 2.5 or more, or 3.0 or more molar excess of amino acids. The use of a stoichiometric excess of amino acids helps ensure the coupling reaction goes to completion and helps the reaction to tolerate excess base from the deprotection reagent.

Coupling completion can be monitored with a qualitative ninhydrin test as described herein. After the coupling is determined to be complete, the coupling reaction mixture is washed with a solvent, and the coupling cycle is repeated for each of the subsequent amino acid residues of the peptide material. Following the final coupling cycle, the resin is washed with a solvent such as NMP, and then washed with an inert second solvent such as DCM.

The inventive methods can be utilized with solid phase or liquid phase synthesis methods, as desired. When utilized in connection with solid phase synthesis, any type of support suitable in the practice of SPPS can be used in accordance with the inventive methods. In preferred embodiments, the support comprises a resin that can be made from one or more polymers, copolymers, or combinations of polymers such as polyamide, polysulfamide, substituted polyethylenes, polyethylene glycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can include linkers that are photocleavable, TFA-cleavable, HF-cleavable, fluoride ion-cleavable, reductively-cleavable, Pd(O)-cleavable, nucleophilically-cleavable, or radically-cleavable. Preferred linking moieties are cleavable under conditions such that the cleaved peptide is still substantially protected by side chain protecting groups.

Preferred solid supports include acid sensitive solid supports, for example, hydroxymethyl-polystyrene-divinylbenzene polymer resin ("Wang" resins, see Wang, S. S. 1973, J. Am. Chem. Soc., 95:1328-33), 2-chlorotrityl chloride resin (see Barlos et al. (1989) Tetrahedron Letters 30(30):3943-3946), and 4-hydroxymethyl-3-methoxyphenoxybutyric acid resin (see Richter et al. (1994), Tetrahedron Letters 35(27): 4705-4706), as well as functionalized, crosslinked poly N-acryloylpyrrolidone resins, and chloromethylpolystyrene dinvinylbenzene polymer resins. These types of solid supports are commercially available from, for example, Calbiochem-Novabiochem Corp., San Diego, Calif.

General procedures for production and loading of resins that can be utilized in SPPS are described in "Principles and Practice of Solid Phase Peptide Synthesis" (Edited by Greagory A. Grant, 1992, W. H. Freeman and Company) and references therein, and are well known to those of ordinary skill in the art. Specific procedures for loading of Wang resins are described for example in Sieber (1987) Tet. Lett. 28:6147-50, and Granadas et al. (1989), Int. J. Pept. Protein Res. 33:386-90.

Once the reactive peptide fragment reacts with the deprotected N-terminal functionality of the peptide fragment, a longer, N-terminal protected peptide fragment is formed. If the desired length peptide is achieved, the synthesis can stop at this point, and the longer peptide fragment can be recovered by any suitable methods. Alternatively, if a longer peptide fragment is desired, the following steps can be repeated in cycles: (i) removing the base-sensitive, N-terminal protecting group from the peptide fragment using a deprotection reagent comprising a base; removing the base from the composition to provide a desired residual base content; and (iii) causing a reactive peptide fragment having a reactive C-terminus and a base-sensitive, N-terminal protecting group to react with the deprotected N-terminal functionality of the peptide fragment under conditions such that the reactive peptide fragment is added to the peptide fragment can be repeated several times, depending upon the peptide to by synthesized. The number of cycles of steps (i) through (iii) can be repeated as desired, to achieve the desired peptide product.

The invention will now be described with reference to the following non-limiting examples.

EXAMPLE

For the following example, the following standard reagents and nomenclature are adopted:

Chloranil test: The chloranil test solution was prepared by adding a drop of a saturated solution of chloranil in toluene to about 1 ml of acetone. The NMP washings were tested by adding a drop of the washing to the chloranil test solution. A blue or violet color is a positive indication for the presence of secondary amine, indicating that Fmoc by-products and/or residual piperidine are still present.

Ninhydrin test: In the qualitative ninhydrin test, a 2-20 mg sample of the resin was withdrawn and washed with NMP and subsequently DCM or methanol. Three drops of a 76% solution of phenol in ethanol, six drops of a 0.2 mM KCN solution in pyridine, and three drops of a 0.28 M solution of ninhydrin in ethanol were added to the sample, and the sample was placed in a heating block at about 100° C. for about 5 minutes. The sample was removed and immediately diluted with an ethanol/water solution (9:1). A blue or violet color is a positive indication of the presence of free amines, including that the reaction is not yet complete. If a positive ninhydrin test was observed after one hour of coupling reaction, the coupling reaction was continued for an additional hour. If a positive ninhydrin test occurred after 3 hours of coupling reaction, the vessel was drained, and the coupling was repeated using about one equivalent of activated amino acid and reagents.

Example 1

Decreased Starting Material

This Example illustrates synthesis of peptide utilizing a decreased amount of deprotection reagent (5% piperidine).

Solid phase synthesis was utilized to prepare the following peptide intermediate:

Ac-Asp-Lys-Trp-Ala-Ser-Leu-Trp-Asn-Trp-OH (SEQ ID NO: 17)

L-Trp(Boc) loaded resin (10 g) was washed with 100 mL $CH_2Cl_2$ and 100 mL NMP.

Meanwhile, a solution of activated amino acid was prepared. Fmoc-L-AsnTrt(OH) (1.5 equivalent), HOBt (1.5 equivalent) and DIEA (1.7 equivalent) were dissolved in NMP (40 mL). The solution was cooled to about 0° C. and a solution of HBTU (1.5 equivalent) in NMP (24 mL) and $CH_2Cl_2$ (18 mL) was added to form the activated amino acid reagent solution.

The activated amino acid reagent solution was then added to the resin, and the suspension was heated to 25-30° C. The suspension was agitated for 1-3 h, until reaction completion (established using the Ninhydrin test). The resin was washed with NMP (2×100 mL).

The resin was then treated with 50 mL of a solution of 5% piperidine in NMP. After stirring for 30 minutes, the resin was drained and again treated with 50 mL of a solution of 5% piperidine in NMP for 30 minutes. HPLC analysis showed complete deprotection. Analysis demonstrated that after the first 30 minutes exposure to 5% piperidine/NMP, the deprotection was more than 99.5% complete.

The resin was washed with NMP (7×70 mL) until a negative chloranil test was observed. The above sequence of amino acid activation and deprotection was then repeated for each amino acid in the sequence (Fmoc-L-Trp(Boc)-OH, Fmoc-L-Leu-(OH), Fmoc-L-Ser(tBu)-OH, Fmoc, L-Ala-OH, Fmoc-L-Trp(Boc)-OH, Fmoc-L-Lys(Boc)-OH, Fmoc-L-Asp(OtBu)OH).

The peptide was cleaved off the resin using TFA and isolated utilizing standard techniques. Peptide yield was 73%, and product purity (measured by HPLC) was 91.8%.

Additional procedures involved in the solid phase, solution phase, and/or hybrid synthesis of peptides are discussed in the following U.S. provisional applications: (1) U.S. provisional application No. 60/533,655, filed Dec. 31, 2003, titled "Methods For Recovering Cleaved Peptide From A Support After Solid Phase Synthesis" bearing, in the names of inventors including Robert Orr Cain; (2) U.S. provisional application No. 60/533,653, filed Dec. 31, 2003, titled "Process and Systems for Recovery of Peptides" bearing, in the names of inventors including Hiralal Khatri; (3) U.S. provisional application No. 60/533,691, filed Dec. 31, 2003, titled "Peptide Synthesis Using Filter Decanting" bearing, in the names of inventors including Mark A. Schwindt; and (4) U.S. provisional application No. 60/533,710, filed Dec. 31, 2003, titled "Peptide Synthesis and Deprotection Using a Cosolvent" bearing, in the names of inventors including Mark A. Schwindt.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

The invention claimed is:

1. A method of synthesizing a peptide, comprising steps of:
   a. providing a composition comprising a peptide fragment, wherein the peptide fragment comprises at least one amino acid residue and includes a base-sensitive, N-terminal protecting group;
   b. removing the base-sensitive, N-terminal protecting group from the peptide fragment using a deprotection reagent comprising a base, whereby an N-terminal functionality on the peptide fragment is deprotected;
   c. removing the base from the composition to provide a residual base content of more than 100 ppm;
   d. causing a reactive peptide fragment having a reactive C-terminus and a base-sensitive N-terminal protecting group to react with the deprotected N-terminal functionality of the peptide fragment under conditions such that the reactive peptide fragment is added to the peptide fragment; and
   e. optionally repeating steps (b) through (d) until a desired peptide is obtained.

2. The method according to claim 1 wherein the base-sensitive, N-terminal protecting group is an Fmoc protecting group.

3. The method according to claim 1 wherein the base is piperidine.

4. The method according to claim 3 wherein the base is added in the form of a reagent that includes piperidine in an amount in the range of 5% to 10% on a weight basis.

5. The method according to claim 4 wherein the reagent includes 5% piperidine on a weight basis.

6. The method according to claim 3 wherein the deprotection reagent further comprises NMP, wherein the weight ratio of the NMP to base in the reagent is in the range of 1:50 to 50:1.

7. The method according to claim 1 wherein step (c) comprises removing the base from the composition to provide a residual base content in the composition in the range of 100 ppm to 10,000 ppm.

8. The method according to claim 7 wherein step (c) comprises removing the base from the composition to provide a residual base content in the composition in the range of 500 ppm to 7,000 ppm.

9. The method according to claim 8 wherein step (c) comprises removing the base from the composition to provide a residual base content in the composition in the range of 1,500 ppm to 5,000 ppm.

10. The method according to claim 1 wherein step (e) is repeated until a peptide constituting all or a portion of enfuvirtide is obtained.

11. The method according to claim 1 wherein step (e) is repeated until a peptide comprising SEQ ID NO: 3 is obtained.

12. The method according to claim 1 wherein step (e) is repeated until a peptide comprising SEQ ID NO: 11 is obtained.

13. The method according to claim 1 wherein step (e) is repeated until a peptide comprising SEQ ID NO: 17 is obtained.

14. The method according to claim 1 wherein step (a) comprises providing a peptide fragment comprising more than one amino acid residue.

15. The method according to claim 14 wherein step (d) comprises providing a reactive peptide fragment comprising more than one amino acid residue.

16. The method according to claim 1 wherein step (d) comprises providing a reactive peptide fragment comprising more than one amino acid residue.

17. The method according to claim 1 wherein the peptide fragment is coupled to a solid support.

18. The method according to claim 1 wherein at least step (d) is carried out using a solution phase synthesis technique.

19. A method of synthesizing a peptide, comprising steps of:
   a. providing a composition comprising a peptide fragment, wherein the peptide fragment comprises at least one amino acid residue and includes a base-sensitive, N-terminal protecting group;

b. removing the base-sensitive, N-terminal protecting group from the peptide fragment using a deprotection reagent comprising a base, whereby an N-terminal functionality on the peptide fragment is deprotected;

c. removing the base from the composition to a point where the composition would provide a positive test result if subjected to a chloranil test;

d. causing a reactive peptide fragment having a reactive C-terminus and a base-sensitive N-terminal protecting group to react with the deprotected N-terminal functionality of the peptide fragment under conditions such that the reactive peptide fragment is added to the peptide fragment; and e. optionally repeating steps (b) through (d) until a desired peptide is obtained.

20. The method according to claim 19 wherein the base-sensitive, N-terminal protecting group is an Fmoc protecting group.

21. The method according to claim 19 wherein the base is piperidine.

22. The method according to claim 19 wherein step (e) is repeated until a peptide constituting all or a portion of enfuvirtide is obtained.

23. The method according to claim 19 wherein step (e) is repeated until a peptide comprising SEQ ID NO: 3 is obtained.

24. The method according to claim 19 wherein step (e) is repeated until a peptide comprising SEQ ID NO: 11 is obtained.

25. The method according to claim 19 wherein step (e) is repeated until a peptide comprising SEQ ID NO: 17 is obtained.

26. The method according to claim 19 wherein step (a) comprises providing a peptide fragment comprising more than one amino acid residue.

27. The method according to claim 19 wherein step (d) comprises providing a reactive peptide fragment comprising more than one amino acid residue.

28. The method according to claim 19 wherein step (d) comprises providing a reactive peptide fragment comprising more than one amino acid residue.

29. The method according to claim 19 wherein the peptide fragment is coupled to a solid support.

30. The method according to claim 19 wherein at least step (d) is carried out using a solution phase synthesis technique.

31. A method of synthesizing a peptide, comprising steps of:

a. providing a composition comprising a peptide fragment, wherein the peptide fragment comprises at least one amino acid residue and includes a base-sensitive, N-terminal protecting group;

b. removing the base-sensitive N-terminal protecting group from the amino acid residue using a deprotection reagent comprising a base, whereby an N-terminal functionality on the peptide fragment is deprotected;

c. causing a reactive peptide fragment having a reactive C-terminus and a base-sensitive, N-terminal protecting group to react with the deprotected N-terminal functionality of the peptide fragment under conditions such that the reactive peptide fragment is added to the peptide fragment, wherein the composition has a basic pH during the reaction of the reactive peptide fragment and the peptide fragment; and d. optionally repeating steps (b) and (c) until a desired peptide is obtained.

32. The method according to claim 31 wherein the composition has a moderately basic pH during the reaction of the reactive peptide fragment with the peptide fragment.

33. The method according to claim 31 wherein the pH of the composition is in the range of 8-10 during the reaction of the reactive peptide fragment with the peptide fragment.

* * * * *

UNITED STATES PATENT AND TRADEMARK OFFICE
CERTIFICATE OF CORRECTION

PATENT NO.        : 7,439,222 B2
APPLICATION NO.   : 11/021952
DATED             : October 21, 2008
INVENTOR(S)       : Martin R. Guinn et al.

It is certified that error appears in the above-identified patent and that said Letters Patent is hereby corrected as shown below:

In the Title Page

Item (75) Inventors:

Inventor "Hendrick Moorlag" should read -- Hendrik Moorlag --;

Signed and Sealed this

Twenty-seventh Day of January, 2009

JOHN DOLL
*Acting Director of the United States Patent and Trademark Office*